（12） United States Patent
Eljamal et al.

(10) Patent No.: US 6,303,582 B1
(45) Date of Patent: *Oct. 16, 2001

(54) COMPOSITIONS AND METHODS FOR NUCLEIC ACID DELIVERY TO THE LUNG

(75) Inventors: Mohammed Eljamal, San Jose; John S. Patton, San Carlos; Linda Foster, Sunnyvale; Robert M. Platz, Half Moon Bay, all of CA (US)

(73) Assignee: Inhale Therapeutic Systems, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/427,836

(22) Filed: Oct. 26, 1999

Related U.S. Application Data

(63) Continuation of application No. 08/422,563, filed on Apr. 14, 1995, now Pat. No. 5,994,314, which is a continuation-in-part of application No. 08/417,507, filed on Apr. 4, 1995, now abandoned, which is a continuation of application No. 08/044,358, filed on Apr. 7, 1993, now abandoned.

(51) Int. Cl.[7] ............... A61K 48/00; A61K 9/127; A61K 9/16; A61K 31/70; C12N 15/87
(52) U.S. Cl. ............... 514/44; 424/450; 424/489; 424/490; 435/458; 435/459
(58) Field of Search ............... 514/44; 424/450, 424/489, 493, 499; 435/375, 458, 459, 455

(56) References Cited

U.S. PATENT DOCUMENTS

| | | |
|---|---|---|
| 4,830,858 | 5/1989 | Payne et al. . |
| 5,049,388 | 9/1991 | Knight et al. . |
| 5,567,433 | 10/1996 | Collins . |
| 5,811,406 | 9/1998 | Szoka, Jr. et al. . |
| 5,994,314 * | 11/1999 | Eljamal et al. ............... 514/44 |

OTHER PUBLICATIONS

Brown, "Gene therapy 'oversold' by Researchers, Journalists," *The Washington Post* (Dec. 8, 1995) pp. A1, A22.

Felgner et al., "Cationic liposome–mediated transfection," *Nature* (1989) vol. 337:387–388.

Friedmann, T., "Progress toward human gene therapy," *Articles*, (1989) 1275–1281.

Gershon et al., "Mode of formation and structural features of DNA–cationic liposome complexes used for transfection," *Biochemistry* (1993) vol. 32:7143–7151.

Rosenfield et al., "Adenovirus–mediated transfer of a recombinant α1–antitrypsin gene to the lung epithelium in vivo," *Science* (1991) vol. 252:431–434.

Stribling et al., "The mouse as a model for cationic liposome–based aerosolized gene delivery," *Journal of Biopharmaceutical Sciences* (1992) 3(1/2), 255–263.

Underwood et al., "A novel technique for the administration of bronchodilator drugs formulated as dry powders to the anesthetized guinea pig," *Journal of Pharmacological Methods*, (1991) vol. 26:203–210.

* cited by examiner

Primary Examiner—John L. LeGuyader
Assistant Examiner—Thomas G Larson
(74) Attorney, Agent, or Firm—Susan T. Evans; Felissa H. Cagan; Stephen L. Hurst

(57) ABSTRACT

A dry powder composition comprises nucleic acid constructs dispersed within with a hydrophilic excipient material, where the powder particles have an average size in the range from 0.5 μm to 50 μm. Nucleic acid constructs may comprise bare nucleic acid molecules, viral vectors, or vesicle structures. The hydrophilic excipient material will be selected to stabilize the nucleic acid molecules in the constructs, enhance dispersion of the nucleic acid in dry powder aerosols, and enhance wetting of the nucleic acid constructs as they are delivered to moist target locations within the body.

20 Claims, 2 Drawing Sheets

COMPOSITIONS AND METHODS FOR NUCLEIC ACID DELIVERY TO THE LUNG

This application is continuation of application Ser. No. 08/422,563, filed Apr. 14, 1995, now U.S. Pat. No. 5,994,314, which is a continuation-in-part of application Ser. No. 08/417,507, filed on Apr. 4, 1995 abandoned, which was a file wrapper continuation of application Ser. No. 08/044,358, filed Apr. 07, 1993, abandoned the full disclosures of which are incorporated herein by reference.

BACKGROUND OF THE INVENTION

1. Field of the Invention

The present invention relates generally to compositions and methods for delivering nucleic acids to the lungs of humans and other animal hosts. More particularly, the present invention relates to compositions which are formed by incorporating nucleic acid constructs within a hydrophilic excipient matrix. The resulting compositions are then stored and utilized in dry powder form.

A form of human gene therapy which is receiving increasing interest relies on the in vivo delivery of functional nucleic acids, usually structural genes, to certain target cells within a human or other host. The nucleic acids may be incorporated into carriers such as viruses, liposomes, or the like, and will be delivered under conditions which result in uptake of the genes into the target cells, with subsequent expression of the genes for an extended period of time.

Of particular interest to the present invention, it has been demonstrated that nucleic acid constructs can be delivered to the lungs of mice and rats by different routes, including intratracheal administration of a liquid suspension of the nucleic acids and inhalation of an aqueous aerosol mist produced by a liquid nebulizer. Although holding great promise, both methods for the delivery of nucleic acids to the lungs suffer from certain drawbacks. Intratracheal administration is not suitable for routine therapeutic use in humans and has a very low patient acceptability. Moreover, intratracheal instillation often results in very uneven distribution of a dispersion in the lungs, with some regions receiving very little or no material. The use of a liquid nebulizer enjoys higher patient acceptability and achieves better distribution, but requires time-consuming equipment set-up, can require prolonged periods of treatment to achieve an adequate dosage, can inactivate a viral carrier, and can result in undesirable aggregation or degradation of the nucleic acids within the aerosol mist. Aggregated nucleic acids will generally be less suitable for uptake into host target cells.

For these reasons, it would be desirable to provide improved compositions and methods for the aerosol delivery of nucleic acids. The compositions will preferably be in a dry powder form which can be readily dispersed in a flowing air stream to provide a dry aerosol for delivery to a patient. The dry powder formulations will permit delivery of required dosages of nucleic acids in a very rapid manner (typically in several or fewer breaths) and will be suitable for storage over extended periods. The dry powders are delivered to particular target regions within the host and are readily dispersed over the internal surfaces of lung, where the powder dissolves in the moist layer over the surfaces to thereby release nucleic acids to interact with the target cells.

2. Description of the Background Art

Stribling et al. (1992) J. BIOPHARM. SCI. 3:255–263, describes the aerosol delivery of plasmids carrying a chloramphenicol acetyltransferase (CAT) reporter gene to mice. The plasmids were incorporated in DOTMA or cholesterol liposomes, and aqueous suspensions of the liposomes were nebulized into a small animal aerosol delivery chamber. Mice breathing the aerosol were found to at least transiently express CAT activity in their lung cells. Rosenfeld et al. (1991) SCIENCE 252:431–434, describes the in vivo delivery of an α1-antitrypsin gene to rats, with secretion of the gene product being observable for at least one week. An adenoviral vector containing the gene was diluted in saline and instilled directly into the rat trachea. Underwood et al. (1991) J. PHARMACOL. METH. 26:203–210, describes the administration of dry powder bronchodilators in a lactose carrier to pig lungs. U.S. Pat. No. 5,049,388 describes the delivery of liquid aerosols containing liposomes to the lungs. Friedman (1989) SCIENCE 244:1275–1281 is a review article describing human gene therapy strategies. In Felgner and Ringold (1989) NATURE 387–388, it is described that the presence of certain polyvalent ions can reduce transfection efficiency in vitro using liposomes. Gershon et al. (1993) BIOCHEMISTRY 32:7143–7151 describe that multivalent anions such as citrate or phosphate can induce fusion of positively-charged liposomes used for transfection.

SUMMARY OF THE INVENTION

In one aspect, the present invention is directed to dry powder nucleic acid compositions comprising nucleic acid constructs (typically small particles) dispersed within a matrix of hydrophilic excipient material to form large aerosol particles. Usually, the nucleic acid particles will be present in excess powdered excipient material, usually being the same excipient which forms the matrix. The powdered aerosol particles will have an average particle size in the range from 0.5 μm to 200 μm, usually being in the range from 0.5 μm to 5 μm for lung delivery with larger sizes being useful for delivery to other moist target locations. The nucleic acid constructs may comprise bare nucleic acid molecules, viral vectors, associated viral particle vectors, nucleic acids present in a vesicle, or the like.

The dry powder nucleic acid compositions may be prepared by suspending the nucleic acid constructs in an aqueous solution of the hydrophilic excipient and drying the solution to produce a powder comprising particles of the nucleic acid construct dispersed within the dried excipient material, usually in the presence of excess powdered excipient. The weight ratio of nucleic acid construct to hydrophilic excipient in the initial solution is in the range from 2:1 to 1:100, preferably from 1:1 to 1:10, and the solution may be dried by spraying droplets into a flowing gas stream (spray drying) or by vacuum drying to produce a crude powder followed by grinding to produce a final powder.

In the case of particles intended for lung delivery, having a particle size from 0.5 μm to 5 μm, each particle may contain from 10 to $10^7$ nucleic acid constructs, usually from $10^2$ to $10^5$ nucleic acid constructs, and preferably from $10^3$ to $10^4$ nucleic acid constructs. The constructs may be uniformly or non-uniformly dispersed in each particle, and the particles in turn will often be present in excess powdered excipient, usually at a weight ratio (nucleic acid construct:excipient powder free from nucleic acids) in the range from 1:1 to $1:10^3$, and more usually from 1:10 to 1:500.

In a preferred embodiment of the present invention, aqueous solutions will contain as the nucleic acid construct, nucleic acids in liposome vesicles. Preferably, such solutions will be substantially free from buffering agents and salts. It has been found that drying, particularly spray drying, of such buffer-free solutions results in powders having enhanced transfection activity compared to powders formed by drying the same liposome vesicles in buffered solutions. In contrast, aqueous solutions in which the nucleic acid constructs comprise viral vectors usually will be buffered to enhance stability of the viral vectors.

In a second preferred aspect of the present invention, the dry powder nucleic acid compositions will be prepared by spraying droplets of the liquid solution into a heated gas stream over a short time period, typically at temperatures ranging from 50° C. to 150° C. over a period from 10 msec to 100 msec, in a spray dryer. The resulting powder comprising particles containing nucleic acid constructs (and usually containing powdered excipient free from nucleic acids) will then be collected in a partially cooled environment, typically maintained at 5° C. to 50° C., and thereafter stored at a temperature from 5° C. to 25° C. at a low humidity, typically below 5% RH. It has been found that such collection and storage conditions help to preserve and stabilize the compositions and to enhance transfection efficiency.

Methods for delivering nucleic acid constructs according to the present invention comprise directing the dry powder containing the nucleic acid constructs to a moist target location in a host, where the hydrophilic excipient matrix material of the particles will dissolve when exposed to the moist target location, leaving the much smaller nucleic acid construct particles to freely interact with cells. In a preferred aspect of the present invention, the target location is the lung and the particles are directed to the lung by inhalation.

Compositions of the present invention are particularly advantageous since the hydrophilic excipient will stabilize the nucleic acid constructs for storage. Excess powdered hydrophilic excipient can also enhance dispersion of the dry powders into aerosols and, because of its high water solubility, facilitate dissolution of the composition to deposit the nucleic acid constructs into intimate contact with the target membranes, such as the lung surface membrane of the host.

DESCRIPTION OF SPECIFIC EMBODIMENTS

Figure 1:
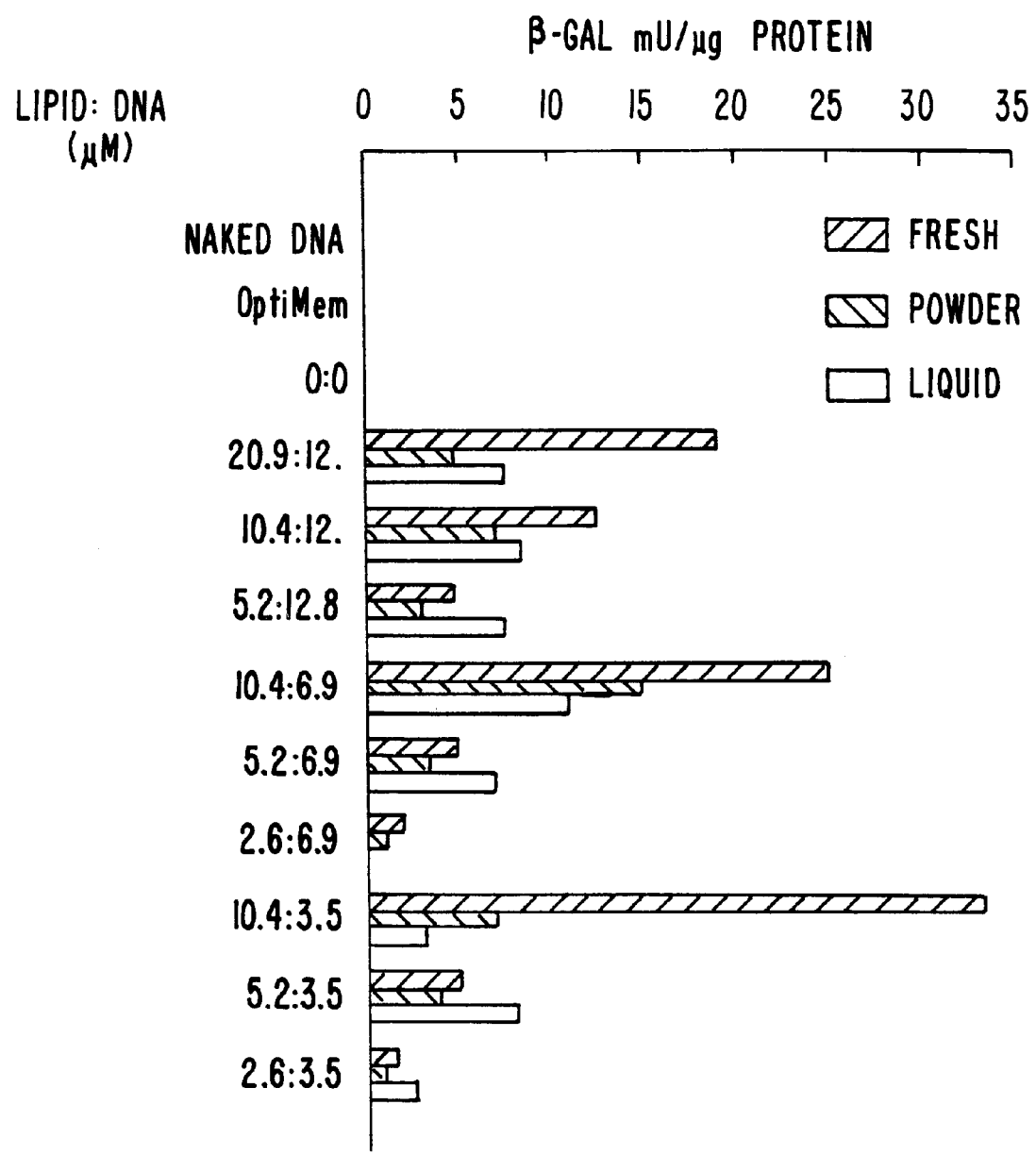
FIG. 1 is a graphical representation of transfection of CFT1 cells with representative cationic lipid:DNA formulations (powder, liquid, freshly-prepared liquid). Relative lipid:DNA concentrations for Tris/mannitol/human serum albumin formulations are provided on the x axis; β-galactosidase activity is indicated on the y axis.

The nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency, wherein the delivery vehicle will be dispersed within larger particles comprising a dried hydrophilic excipient material.

A first type of such delivery vehicles comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) CIRC. RES. 71:1508–1517, the disclosure of which is incorporated herein by reference. A suitable adenovirus gene delivery system is described in Rosenfeld et al. (1991) SCIENCE 252:431–434, the disclosure of which is incorporated herein by reference. Both retroviral and adenovirus delivery systems are described in Friedman (1989) SCIENCE 244:1275–1281, the disclosure of which is also incorporated herein by reference.

A second type of nucleic acid delivery vehicle comprises liposomal transfection vesicles, including both anionic and cationic liposomes. The use of anionic liposomes requires that the nucleic acids be entrapped within the liposome. Cationic liposomes do not require nucleic acid entrapment and instead may be formed by simple mixing of the nucleic acids and liposomes. The cationic liposomes avidly bind to the negatively charged nucleic acid molecules, including both DNA and RNA, to yield complexes which give reasonable transfection efficiency in many cell types. See, Farhood et al. (1992) BIOCHEM. BIOPHYS. ACTA. 1111:239–246, the disclosure of which is incorporated herein by reference. A particularly preferred material for forming liposomal vesicles is lipofectin, which is composed of an equimolar mixture of dioleylphosphatidyl ethanolamine (DOPE) and dioleyloxypropyl-triethylammonium (DOTMA), as described in Felgner and Ringold (1989) NATURE 337:387–388, the disclosure of which is incorporated herein by reference.

It is also possible to combine these two types of delivery systems, i.e., lipids and viral vectors. For example, Kahn et al. (1992), supra., teaches that a retrovirus vector may be combined in a cationic DEAE-dextran vesicle to further enhance transformation efficiency. It is also possible to incorporate nuclear proteins into viral and/or liposomal delivery vesicles to even further improve transfection efficiencies. See, Kaneda et al. (1989) SCIENCE 243:375–378, the disclosure of which is incorporated herein by reference.

Hydrophilic excipient materials suitable for use in the compositions of the present invention will be able to form a dried matrix in which the nucleic acid constructs are dispersed in order to stabilize the nucleic acid molecules during storage, facilitate dispersion of the nucleic acids in dry powder aerosols, and enhance wetting and subsequent contact of the nucleic acids with the moist target locations within a patient or other treated host. A sufficient amount of hydrophilic excipient will be present to form a dry powder matrix in which the nucleic acids are dispersed, typically being present in the resulting particles at a weight ratio (nucleic acid construct:particle) in the range from 1:1 to 1:1000, usually from 1:10 to 1:500. Suitable hydrophilic excipient materials include those listed in Table 1.

| TYPE OF HYDROPHILIC MATRIX MATERIAL | EXAMPLES |
| --- | --- |
| Proteins and Peptides | Human serum albumin; Collagens; Gelatins; Lung surfactant proteins; and fragments thereof. |
| Hyaluronic acid | Hyaluronic acid. |
| Sugars | Glucose; Lactose; Sucrose, Xylose; Ribose; and Trehalose. |
| Sugar alcohols | Mannitol. |
| Oligosaccharides | Raffinose and Stachyose. |
| Other carbohydrates | Dextrans; Maltodextrans; Dextrins; Cyclodextrins; Maltodextrins; Cellulose; and Methylcellulose. |
| Amino acids | Glycine; Alanine; and Glutamate. |
| Organic acids and salts[1] | Ascorbic acid; Ascorbate salts; Citric acid; and Citrate salts. |
| Inorganic salts[1] | NaCl; NaHCO$_3$; NH$_4$HCO$_3$; MgSO$_4$; and Na$_2$SO$_4$. |

[1]The use of organic acids and salts, and inorganic salts, as a matrix material is less preferred in the case of liposomal transfection vesicles, where the salts and acids can interfere with the stability of the vesicle.

The dry powder formulations of the present invention may conveniently be formulated by first suspending the nucleic acid constructs, which are generally insoluble in water, in aqueous solutions of the hydrophilic excipient. The relative amounts of nucleic acid construct and hydrophilic excipient material will depend on the desired final ratio of nucleic acid to excipient. Conveniently, the ratio of nucleic acid construct to excipient will be in the range from about 2:1 to 1:100 (nucleic acid:excipient), preferably from 1:1 to 1:10, with a total solids concentration in the aqueous suspension being usually less than 5% by weight, more usually being less than 3% by weight.

In the case of nucleic acid constructs comprising liposomal transfection vesicles, the aqueous solutions are preferably free from polyvalent buffering agents (particularly citrate and phosphate), salts, and other negatively charged species (other than the nucleic acids and in some cases the hydrophilic matrix material), which have been found in some cases to reduce transfection efficiency of the resulting dried powders. It is presently believed that such charged species will interact with the liposomal constructs in a deleterious manner as the compositions are dried.

In the case of nucleic acid constructs comprising viral vectors, it is usually desirable that the aqueous solution be buffered in order to enhance the activity of the viral vectors after drying.

The aqueous solution can then be spray dried under conditions which result in a powder containing particles within a desired size range, typically but not necessarily having a mean particle diameter in the range from about 0.5 μm to 50 μm, with the precise particle size depending on the eventual use. For lung delivery, the particle size will typically be in the range from 0.5 μm to 10 μm, usually being from 0.5 μm to 7 μm, and preferably from 1 μm to 4 μm. The mean particle diameter can be measured using conventional equipment such as a Cascade Impactor (Andersen, Ga.).

Higher total solids concentrations within the aqueous solution will generally result in larger particle sizes. Powders having an average particle size above 10 μm, usually in the range from about 20 μm to 50 μm, can be thus formed, and are particularly useful for nasal, dermal, surgical, and wound applications where it is desired that the powder rapidly settle on a target location.

Dry powders can also be formed by vacuum drying, either at room temperature or under freezing temperatures (lyophilization). Usually, it will be desirable to start with an aqueous solution having higher total solids content, typically above 0.1% by weight, more typically above 0.2% by weight. For smaller particles having a size from 0.5 μm to 10 μm, the liquids will usually have an initial solids content from 0.2% to 1% by weight. For larger particles of 10 μm and above, the solids content will usually be from 15% to 10% by weight. The vacuum drying results in a crude powder which can then be further ground, typically by jet milling, to produce a product having a uniform particle size and a desired particle size, typically within the 1 μm to 50 μm range set forth above.

Specific methods for preparing dry powders of a type which are useful in the present invention are described in copending application Ser. No. 08/423,515, the full disclosure of which is incorporated herein by reference.

The dry powder compositions of the present invention are suitable for delivery to a variety of target locations within a patient or other treated host, with moist membrane locations, such as the lungs, nasal membranes, mouth, throat, stomach, intestines, vagina, and the like being preferred. The compositions may also be used to deliver the nucleic acid constructs to the subcutaneous or intramuscular compartment by dry powder injection, or to open wounds, including surgical wounds, in order to deliver genes to exposed tissue.

In the case of delivery to the lungs, the dry powders will have a mean particle diameter in the range from about 1 μm to 5 μm, and may be efficiently dispersed and delivered in a flowing gas stream for inhalation by the patient or host.

A particularly suitable device for dry powder delivery is described in copending application Ser. No. 07/910,048, assigned to the assignee of the present application, and filed on Jul. 8, 1992, the full disclosure of which is incorporated herein by reference.

The following examples are offered by way of illustration, not by way of limitation.

EXAMPLES

Materials and Methods

Lipids

1. DMRIE:DOPE (50/50, mole ratio, Vical, San Diego, Calif.). The lipids (DMRIE:DOPE) were formulated to generate 1.56 mM solution by resuspending 5 mg vial in 2.4 ml de-ionized water and vortexing at full speed for 1 minute.
2. DOTMA/DOPE (50:50, mole ratio, Megabios, San Francisco, Calif.).

DNA Plasmid 1. pCMVβ (Genzyme, Framingham, Mass.). pCMV-β-gal: Cytomegalovirus promoter was linked to the *Escherichia coli* Lac-Z gene, which codes for the enzyme β-galactosidase. The activity of this enzyme was visualized with the reagent X-gal (b-D-galactoside). The DNA plasmid (pCMVβ, 4.26 mg/ml) was formulated to generate 960 μM by adding 0.145 ml of the DNA suspension to 1.9 ml 1 mM tris buffer, pH 8.

2. pCIS-CAT (Megabios, San Francisco, Calif.). pCIS-CAT: Chloramphenicol acetyltransferase (CAT) fused to the human cytomegalovirus (CMV) immediate early promoter/enhancer element.

Lipid:DNA Complex

The complex was formed by first adding DNA plasmids (pCMVβ, as described above) to a certain volume of bulking and excipient materials solution to attain the desired concentration. The preformed lipids (DMRIE:DOPE) were added to form the complex at least 10 minutes prior to processing into powder. The lipid:DNA ratio was molar.

Virus

Ad2-CMV-LacZ-2 (Genzyme, Framingham, Mass.). AD2-CMV-Lac-Z: Cytomegalovirus promoter was linked to the *Escherichia coli* Lac-Z gene and was incorporated into replication deficient recombinant virus. Takiff et al. (1984) J. VIROL. 51:131–136 and Gilardi et al. (1990) FEBS LETT. 267:60–62.

1 mM Tris Buffer pH 8 (0.14 mg/ml Solids)

(1) Dissolved 60.6 mg Tris base (J T Baker, lot # x171-07) in 500 ml deionized house water to make a 1 mM solution. (2) Dissolved 78.8 mg Tris HCl (J T Baker, lot # 4103-1) in 500 ml deionized house water to make a 1 mM solution. To the magnetically stirred Tris base solution, Tris HCl was slowly added to obtain pH 8.

Tris/Mannitol/HSA (5.07 mg/ml Solids)

Dissolved 1,363.0 mg mannitol (Mallinckrodt, lot # 6208 KLRP) and 156.7 mg HSA (Miles, lot # 204) in 300 ml of the 1 mM Tris buffer.

Glycine/HSA (I) (5.44 mg/ml Solids)

Dissolved 60.6 mg HSA and 1,028.0 mg glycine (J T Baker, Lot # A28732) in 200 ml filtered and deionized house water, pH 6.4.

Glycine/Mannitol/HSA (5.57 mg/ml Solids)

Dissolved 50.6 mh HSA, 540.0 mg glycine and 524.0 mg mannitol in 200 ml of filtered and deionized house water, pH 6.4.

Phosphate Buffer (PB) pH 7.4 (1.89 mg/ml Solids)

Dissolved 200.1 mg KCl (J T Baker, Lot No. 3040-01), 1,451.4 mg $Na_2HPO_4 \cdot 7H_2O$ (Mallinckrodt, Lot No. 7896 KJPE) and 242.1 mg $KH_2PO_4$ (J T Baker, Lot No. 3246-01) in one liter of the house deionized water to make pH 7.4.

Phosphate/HSA (3.93) mg/ml Solids)

Dissolved 203.8 mg HSA (Miles, Lot No. 204) in 100 ml of the phosphate buffer pH 7.4.

Mannitol/HSA in PB (60.05 mg/ml Solids)

Dissolved 1,403.1 mg mannitol (Mallinckrodt, Lot No. 6208 KLRP) in 25 ml phosphate/HSA. Stored below 5° C.

Glycine/HSA (I) in PB (28.40 mg/ml Solids)

Dissolve 611.8 mg glycine (J T Baker, Lot No. 0581-01) in 25 ml phosphate/HSA. Stored below 5° C.

Glycine/HSA (II) in PB (10.5 mg/ml Solids)

Dissolved 613.8 mg glycine (J T Baker, Lot No. 0581-01) and 1 ml (250 mg) HSA (Alpha Therapeutic, lot # NB2049A) in 100 ml phosphate/HSA. Stored below 5° C.

Glycine/HSA (II) in Water (8.6 mg/ml Solids)

Dissolved 612.4 mg glycine (J T Baker, Lot No. 0581-01) and 1 ml (250 mg) HSA (Alpha Therapeutic, lot # NB2049A) in 100 ml de-ionized water. Stored below 5° C.

Mannitol/Glycerine/HSA in PB (45.09 mg/ml Solids)

Dissolved 700.2 mg mannitol (Mallinckrodt, Lot No. 6208 KLRP) and 328.8 mg glycine (J T Baker, Lot No. 0581-01) in 25 ml of phosphate/HSA. Stored below 5° C.

Adenovirus (40.20 mg/ml)

Dissolved 305.3 mg sucrose (Sigma, Lot No. 69F0026), 77.9 mg NaCl (VWR SCI., Lot No. 34005404) and 0.1 ml of Ad2-CMV-LacZ virus ($10^{11}$ iu/ml with particle concentration of $\sim 5 \times 10^{12}$/ml in PBS+3% sucrose, Genzyme) in 10 ml phosphate buffer. This solution was prepared and used cold on the same day and was stored frozen at −70° C. Also, it was used again 10 weeks later, it underwent only one freeze/thaw cycle.

Powder Processing

All the powders were processed in a Buchi-190 mini spray dryer. Briefly, the solution is atomized into liquid droplets and is dried to solid particulate with adjunct stream of air heated to a specified temperature (inlet temperature). The airborne particulate are fed into a cyclone (outlet temperature) where they are separated from the air into a collection cup.

Dispersibility

Dispersibility of the dry powder was determined using a dry powder inhaler (generally as described in application Ser. No. 08/309,691, the full disclosure of which is incorporated herein by reference) or a test bed. Briefly, a blister pack filled with 5.0±0.5 mg powder was loaded and dispersed in the device. The resulting aerosol cloud in the device chamber was immediately drawn at a suction flow-rate of 30 LPM for 2.5 seconds and was collected on a 47 mm, 0.65 μm pore size, polyvinylidene fluoride membrane filter (Millipore). Dispersibility is the fraction of powder mass collected on the filter relative to mass filled into the blister pack.

Particle Size (Horiba)

The particle size distribution (PSD) of the powder samples was measured using the Horiba CAPA-700 centrifugal sedimentation particle size analyzer. Approximately five mg of powder was suspended in approximately 5 ml of Sedisperse A-11 (Micromeritics, Norcoss, Ga.) and briefly sonicated before analysis. The instrument was configured to measure a particle size range of 0.4 to 10 μm in diameter, and the centrifuge was operated at 2000 rpm. The particle size distribution was characterized by mass median diameter, and by the mass fraction less than 5.0 μm.

Particle Size (Cascade Impactor)

The particle size distribution of aerosolized powders (aerosol from blister using prototype 1B device) was obtained using an IMPAQ 6-stage (16, 8, 4, 2, 1, 0.5 μm cut off diameters) cascade impactor (California Measurement, Sierra Madre, Calif.). A glass Throat, described in the *European Pharmacopoeia,* was fitted over the intake of the cascade impactor. The glass throat was designed to simulate particle deposition in the human throat when aerosol is sampled in the cascade impactor. The impactor airflow was set to 14.5 LPM, the calibrated operating flow of the instrument. To measure the particle size of the aerosol, a blister pack filled with approximately 5 mg of powder was loaded into the prototype inhaler, the device was actuated and the aerosol cloud drawn from the chamber into the glass throat/cascade impactor set up. The particle size was determined gravimetrically by weighing the powder on the glass throat, impactor plates and the backup filter and plotting the results on a log-probability graph. The mass median aerodynamic diameter (MMAD) and the mass fraction less than 5 μm were determined from the graph.

Example 1

Spray Dried Powder Preparation: Adenoviral Vector (CFTR Gene)/Mannitol Formulation A respirable powder incorporating the human cystic fibrosis transmembrane conductance (CFTR) gene and having a particle diameter from 1 μm to 5 μm is formed as follows. The CFTR gene is linked to the adenovirus (Ad) late promoter, and the resulting expression cassette is incorporated into an adenovirus vector, as taught in Rosenfeld et al.

(1991) SCIENCE 252:431–434. The adenovirus vector has a deletion in the E3 region, thus permitting encapsidation of the recombinant genomic DNA including the CFTR gene. The vector further has a deletion in the Elq region, preventing viral replication.

Sufficient adenovirus vector is added to a phosphate buffered saline solution (0.15 mM NaCl, 2.7 mM KCl, 8.1 mM $Na_2PO_4$, 1.5 mM $KH_2PO_4$, pH 7.2) containing 5 mg/ml mannitol at 4° C. to provide approximately $10^8$ plaque forming units (pfu)/ml. The resulting solution is spray dried in a commercially available drier from suppliers such as Buchi and Niro.

After spray drying, the powder is collected and stored at less than 10% relative humidity. The powder may be incorporated into inhalation delivery devices as described in copending application Ser. No. 07/910,048.

Example 2
Spray Dried Powder Preparation: DOTMA/DOPE Liposomes with α-1AT-Gene/Maltodextrin Formulation A respirable powder incorporating the α1-antitrypsin (α1AT) gene and having a particle diameter in the range from 1 μm to 5 μm is formed as follows.

A plasmid vector carrying the α1AT gene is prepared as described in Gormon et al. (1982) PNAS 79:6777–6781 and Sambrook et al. (1989), MOLECULAR CLONING: A LABORATORY MANUAL, Cold Spring Harbor Laboratory, Cold Spring Harbor, N.Y. The α1AT gene is fused to the human cytomegalovirus (CMV) immediate early promoter/enhancer element. The plasmid is then purified by alkaline lysis and ammonium acetate precipitation, and the nucleic acid concentration is measured by UV absorption.

Plasmid DNA (0.75 mg/ml) is dispersed in an aqueous solution of double distilled water containing 1.35 mg/ml of DOTMA/DOPE liposomes at a 1:1 molar ratio. The resulting mixture is sonicated for 20 minutes in a water bath. Maltodextrin is added to the mixture after sonication at a concentration of 5 mg/ml. The mixture is then spray dried as described in Example 1.

Example 3
Freeze-Dried Powder Preparation: Cationic Fusogenic Liposomes with α-1AT/HSA Formulation Plasmid DNA (0.75 mg/ml), prepared as described in Example 2, is mixed with a multilamillar dispersion of cationic fusogenic liposomes (1.5 mg/ml) by gentle agitation at 23° C. for 24 hours in a solution containing 10 mg/ml human serum albumin (HSA). The solution is freeze dried in trays, and the resulting powder is jet milled with high purity nitrogen in a conventional jet mill until a mass median aerodynamic diameter of 1 μm to 4 μm is achieved. The resulting respirable powder is stored at less than 10% relative humidity until it is needed for dispersion in a dry powder device for inhalation.
Transfection of Cells with Lipid:DNA Complexes and Adenovirus Vectors Example 4
Lipid:DNA Constructs Useful for Gene Therapy: Transfection of CFT1 Cells with Various Cationic Lipid:DNA Formulations and Dry Powder Characterization
4.A. Cationic Liposome Dry Powder Formulations (Absent Nucleic Acid)

The following formulations were made to develop aerosol liposomes in dry powder form. Cationic lipid (34.5 mg (25 μMoles) DOTMA:DOPE, 1:1, Megabios) was dispersed in 100 ml of 6.75 mg/ml mannitol solution. This solution (7.1 mg/ml solids) was processed into powder according to the following spray drying parameters:

Solution feed rate: 5.8 ml/min
Inlet/Outlet Temperatures: 137/73° C.
Atomizer air flow rate: 800 LPH The powder yield was about 6% and could not be filled into blister packs. The resulting powder was sticky, possibly due to the presence of liposomes on the surface of the powder. The observed stickiness may have resulted from the cationic liposomes on the surface of the dry particles strongly interacting with each other. In order to solve this problem, human serum albumin (HSA) was added to the solution to increase the dispersibility of the powder by modifying its surface morphology.

Two liquid formulations containing HSA (Alpha Therapeutic, 12.5 g/50 ml solution), lipids (DOTMA:DOPE) and mannitol were dried in the Buchi-190 spray dryer. The liquid solution was fed at 3 ml/min and the inlet/outlet temperatures ranged between 95–105° C./55–70° C. It was found that both the yield and the dispersibility of the dry powder were improved with the addition of HSA (see Table 1).

TABLE 1

Summary of Lipids/Mannitol aerosol formulations.

| Formula No. | Composition HSA/Lipids/Mannitol (mg/ml) | Yield Percent | Dispersibility Percent |
|---|---|---|---|
| 1 | 0.00/0.35/6.75 | 6 | — |
| 2 | 0.40/0.35/6.40 | 55 | 36 ± 6 |
| 3 | 0.91/0.35/6.40 | 54 | 59 ± 4 |

4.b. Plasmid DNA Powder Formulation

To investigate whether this process would preserve the integrity of DNA molecules, pCMVβ in Tris/Mannito/HSA solution (7.5 mg/ml solids) was spray dried according to the following conditions:

Solution feed rate: 4.3 ml/min
Inlet/Outlet Temperatures: 120° C./70° C.
Atomizer air flowrate: 800 LPH The resulting powder was reconstituted in de-ionized water and was analyzed by gel electrophoresis (1.3% agrose in 0.5×TBE plus 0.5 μg/ml ethidium bromide, 100 volts for four hours). Unprocessed DNA molecules were also run in the same gel. The powder was tested for transfection activity in vitro as described under Example 4D.

Similar bands were observed for both processed and unprocessed DNA in the gel electrophoresis. As expected, the reconstituted DNA (without any delivery vehicle, cationic lipid or adenovirus) powder did not show any transfection activity in the in-vitro cytofection assay.
4.C. Dry Powder and Liquid Formulations Containing Cationic Lipids and DNA Three sets of cationic lipid (DMRIE:DOPE):DNA (pCMVβ) formulations were prepared, processed into dry powders and characterized:

1. DMRIE:DOPE lipids/pCMVβ/Tris-Mannitol-HSA Formulation. The lipid:DNA complex (as described in the Materials and Methods section) was formed in Tris/mannitol/HSA solution (5.07 mg/ml solids) with the following concentration ratios of lipid:DNA (μM:μM)-0:0, 0:6.9, 20.9:12.8, 10.4:12.8, 5.2:12.8, 10.4:6.9, 5.2:6.9, 2.6:6.9, 0.4:3.5, 5.2:3.5 and 2.6:3.5.

2. DMRIE:DOPE lipids/pCMVβ/Glycine-HSA Formulation (A). The lipid:DNA complex (Materials and Methods section) was formed in glycine/HSA (I) in water (5.44 mg/ml solids) with the following lipid:DNA concentration ratios (μM:μM)-20:20, 20:15, 10:10 and 10:5.

3. DMRIE:DOPE lipids/pCMVβ/Glycine-Mannitol-HSA Formulation (A1). The lipid:DNA complex (Materials and Methods section) was formed in glycine/mannitol/HSA solution (5.57 mg/ml solids) with the following ratios (μM:μM)-20:20, 20:15, 10:15, 10:10 and 10:5. The solutions were processed into powder according to the following spray drying parameters:
Solution feed rate: 3.8 ml/min
Inlet/Outlet Temperatures: 115–125° C./70–85° C.
Atomizer air flowrate: 700–800 LPH Aliquots of liquid formulations and the resulting powders were kept refrigerated and duplicates were sent on ice pack to be assayed for transfection activity in vitro (as described below) and also to be compared with freshly prepared suspensions of Lipid:DNA with similar concentration ratios. Select powders from sets 2 and 3 were characterized using the Horiba, IMPAQ 6-stage cascade impactor and a dry powder inhaler.

4.D. In-Vitro Cytofection Assay: Cell Preparation and Results

Cell Preparation

Cells of choice (CFT1, airway cells from cystic fibrosis patients) were placed into 96-well plates at 20,000/well in growth medium the day before cytofection. Just prior to cytofection, the cells were observed, and approximate confluencey estimated.

Lipid:DNA Preparation

The lipid was formulated to 670 mM and the DNA to 960 mM. The complex was formed by adding the lipid to the DNA for 15 minutes, and then 100 μl of the complex was added to the cells (media previously aspirated). Cytofection occurred over 6 hours before the addition of 50 μl 30% FCS-OPTIMEM. The following day, 100 μl of 10% FCS-OPTIMEM was added to each well. The assay began 48 hours after start of cytofection.

Assay

1. Remove media and wash cells twice with 100 μl PBS.
2. Add 25 μl lysis buffer (250 mM Tris-HCl, pH8.0, and 0.15% Triton X-100) and incubate at RT for 30 minutes.
3. Freeze plate at −70° C. for 20 minutes, thaw at RT for 15 minutes.
4. Break up cells by carefully vortexing plate for 15 seconds.
5. Freeze plate at −70° C. for 20 minutes, thaw at RT for 15 minutes.
6. Add 100 μl PBS followed by 150 μl of CPRG substrate (1 mg/ml chlorophenol red glactopyranoside, 60 mM disodium hydrogen phosphate pH8, 1 mM magnesium sulfate, 10 mM potassium chloride, and 50 mM β-mercaptoethanol)
7. Incubate at 37° C. for 2 hrs until red color develops and read at 580 nm in microplate reader.

Results

Figure 2:
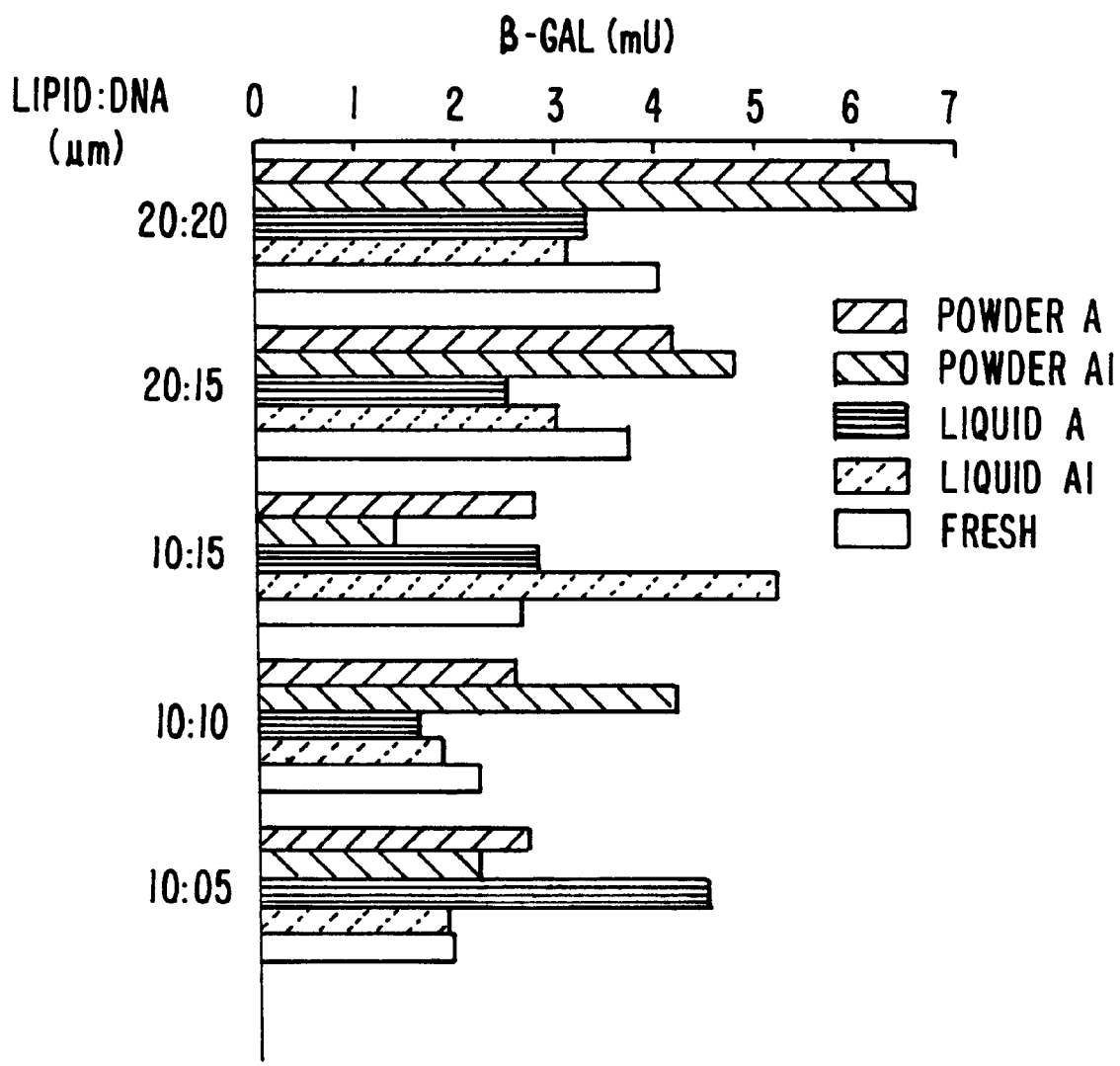
FIG. 2 is a graphical representation of transfection of CFT1 cells using both liquid and powder cationic lipid:DNA formulations (glycine/mannitol/HSA and glycine/HSA) prepared in the absence of Tris buffer. β-galactosidase activity, indicative of transgene expression, is shown on the y axis. Concentration ratios of lipid:DNA for powder, liquid, and freshly-prepared liquid formulations are provided on the x-axis.

A comparison of β-gal expression in vitro (CFT1 cell line) between the various powder and the two liquid (stored control and freshly made control) formulations is shown in FIG. 1 (DMRIE:DOPE lipids/pCMVβ/Tris-Mannitol-HSA Formulation) and in FIG. 2 (DMRIE:DOPE lipids/pCMVβ/Glycine/HSA Formulation(A) and (DMRIE:DOPE lipids/pCMVβ/Glycine/mannitol/HSA Formulation(A1)).

The powders were reconstituted in double distilled de-ionized water. The transfection activities of the liquid and powder formulations of set 1 (DMRIE:DOPE lipids/pCMVβ/Tris-Mannitol-HSA Formulation), which contained the Tris buffer, were considerably less than freshly made liquid formulations (FIG. 1). In the powders which contained no buffer, there was a 75% increase in the transfection activity of the 20:20 and a 30% increase in the 20:15 as compared with liquid formulations (see FIG. 2). The measured physical parameters of the selected powders that showed superior transfection efficiencies are listed in Table 2. The glycine/HSA and glycine/mannitol/HSA powder formulations had similar transfection activities (FIG. 2) but the glycine/HSA powders dispersed better than the glycine/mannitol/HSA (Table 2).

TABLE 2

Lipid:DNA powder physical characteristics.

| Formula ratio | Bulking Material | Dipersi. (% RSD) (n = 3) | HORIBA MMD* | Cascade MMAD** | Impactor % ≦ 5 μm |
|---|---|---|---|---|---|
| 20:20 | Glycine | 61 (20) | 2.0 | 3.9 | 60 |
| 20:15 | Glycine | 64 (1) | 2.0 | 2.4 | 75 |
| 20:20 | Gly/Man | 47 (12) | 2.0 | 3.0 | 70 |
| 20:15 | Gly/Man | 51 (12) | 2.4 | 4.1 | 60 |

*MMD: Mass Median Diameter
**MMAD: Mass Median Aerodynamic Diameter

Example 5

Adenovirus Vector Constructs Useful for Gene Therapy: Dry Powder Aerosols

This study included two sets of experiments. In the first set, the effects of bulking agents in phosphate buffer (PB), (i) mannitol/HSA, (ii) glycine/HSA and (iii) mannitol/glycine/HSA, on the infectivity of adenovirus dry powders were investigated. In the second set, the effects of buffer removal and process outlet temperature on viral infectivity were investigated. All solutions were used and stored cold (about 5° C.).

Set 1. Buffered Formulations Containing Various Excipients (i) Five mannitol/HSA in PB formulations were prepared as follows. To four samples of 4×3 ml mannitol/HSA was added 0.1 ml of adenovirus solution to obtain $3.2\times10^7$ iu/ml and about 60 mg/ml solids. The fifth mannitol/HSA solution was used as a control with no virus. Two of the virus-containing samples were diluted with de-ionized water to about 9 mg/ml solids.

(ii) Two formulations of 6.3 ml glycine/HSA (I) in PB plus 0.4 ml adenovirus solution were prepared (29 mg/ml solids, $6.3\times10^7$ iu/ml). One of the formulations was diluted with de-ionized water to 9 mg/ml solids.

(iii) Two formulations of 4.1 ml mannitol/glycine/HSA in PB plus 0.4 ml of virus solution were prepared (45.1 mg/ml solids, $8.89\times10^7$ iu/ml). One of the samples was diluted with de-ionized water to 9 mg/ml. The adenovirus solution was freshly made on the same day and was kept cold on ice.

Set 2. Comparison of Buffered Versus Unbuffered Solutions of Glycine/HSA

Four formulations were prepared, two contained 25 ml of glycine/HSA (II) in PB plus 0.4 ml of adenovirus solution (10.5 mg/ml, $1.6\times10^7$ iu/ml) and the other two contained 25 ml of glycine/HSA (II) in water plus 0.4 ml of adenovirus solution (8.6 mg/ml, $1.6\times10^7$ iu/ml). The adenovirus solution underwent only one freeze/thaw cycle before usage in the above preparations. It was prepared around 10 weeks ago and was stored frozen at −70° C.

These formulations were processed into powders in the Buchi-190 spray dryer according to the following parameters:

Solution feed rate: 3.5–6.0 ml/min
Inlet/Outlet temperatures: 100–140/70–90° C.
Atomize flowrate: 700–800 LPH The resulting powder was kept refrigerated and was sent for testing on dry ice. Prior to testing for β-gal expression or for virus titers, the powders were reconstituted with phosphate buffered saline (PBS).

Results

None of the mannitol/HSA powder formulations of set one showed any β-gal expression in the standard 6-well test and therefore they were not titered for virus infectivity.

The glycine/HSA (I) and glycine/mannitol/HSA in PB from set one were equal in their β-gal expression and were tittered for virus infectivity. Their titers ranged from 7% to 15% of the expected values. The particle size distribution (HORIBA), dispersibility and the aerodynamic size distribution (IMPAQ 6-stage) are listed in Table 3 for the two glycine/HSA in PB powders.

Set two powders and 0.1 ml of the adenovirus solution (V) frozen to −70° C. were sent on dry ice for titer measurements (Table 4). Powders manufactured with and without the phosphate buffer retained 76–54% and 2–1.4% of their virus infectivities, respectively (Table 4). Lowering the outlet temperature by 5° C. increased the buffered formulation virus infectivity by 22% but it lowered the unbuffered one by 6%.

TABLE 3

Characterization of Set One Powders:
Glycine/HSA in PB adenovirus formulations.

| Formula (mg/ml) | Dipersi. (% RSD) | HORIBA MMD | Cascade impactor MMAD | % < 5 μm | % infectivity retained |
|---|---|---|---|---|---|
| 29 | 40 (25) | 2.6 | 2.8 | 70 | 14 |
| 9 | 51 (1) | 2.3 | 1.8 | 80 | 7 |

TABLE 4

Viral Titer Results: Set Two Adenovirus powders
(glycine/HSA with and without buffer).

| Formulation | Outlet Temp. ° C. | Expected iu/ml | Measured iu/ml |
|---|---|---|---|
| V | N/A | $1.0 \times 10^9$ | $1.6 \times 10^8$ |
| Buffered | 77 | $1.0 \times 10^8$ | $5.4 \times 10^7$ |
| Buffered | 72 | $1.0 \times 10^8$ | $7.6 \times 10^7$ |
| Unbuffered | 77 | $1.0 \times 10^8$ | $2.0 \times 10^6$ |
| Unbuffered | 72 | $1.0 \times 10^8$ | $1.4 \times 10^6$ |

To summarize the representative results described in the above Examples, respirable dry powder aerosols containing lipid:DNA complexes or adenovirus vectors for the delivery of active genes to mammalian cells were prepared and tested. Dispersible dry powders containing either vehicles (i.e., lipid or viral vectors) were made with mannitol and/or glycine as bulking agents and HSA as a surface modifier to help disperse the powders. Transfection activities in CFT1 cells (cells from the airways of cystic fibrosis patients) and virus titers of the resulting powders were measured and compared to liquid controls. The dispersibilities and aerodynamic particle size distributions of select powders that retained their transfection activities were also measured. The transfection activities of the lipid:DNA powders, formulated without buffer, were better than both the liquids they were made of and the freshly prepared liquid formulations. Lipids and DNA were complexed with each other at least 15 minutes prior to cytofection. The titers of the virus in the best powder formulation and its liquid control were 76% and 16% of the expected values, respectively. The dispersibility and the respirable fractions of the selected powders ranged from 40 to 64% and 60 to 80%, respectively. These data demonstrate the ability to obtain respirable and stable dry powder formulations of both cationic lipids complexes and adenovirus delivery systems.

Although the foregoing invention has been described in some detail by way of illustration and example, for purposes of clarity of understanding, it will be obvious that certain changes and modifications may be practiced within the scope of the appended claims.

What is claimed is:

1. A spray dried powder composition comprising a nucleic acid construct dispersed in a hydrophilic excipient.

2. A dry powder composition comprising a nucleic acid construct dispersed in a hydrophilic excipient.

3. A method for preparing the dry powder composition of claim 2, said method comprising:
   (a) suspending a nucleic acid construct in an aqueous solution of an excipient to form a suspension; and
   (b) spraying droplets of the suspension into a heated gas stream to form a dry powder comprising the nucleic acid construct dispersed within the hydrophilic excipient.

4. The method of claim 3, wherein said heated gas stream is at a temperature ranging from about 50° C. to 150° C.

5. The method of claim 3, wherein the weight ratio of nucleic acid construct to hydrophilic excipient in the initial suspension is from 1:1 to 1:10.

6. A dry powder composition produced by the method of claim 3.

7. The composition of claim 1 or claim 2, wherein said nucleic acid construct comprises bare nucleic acid molecules.

8. The composition of claim 1 or claim 2, wherein said nucleic acid construct comprises nucleic acid molecules present in a delivery vehicle.

9. The composition of claim 8, wherein said delivery vehicle comprises liposomal vesicles.

10. The composition of claim 9, wherein the liposomal vesicles comprise anionic liposomes.

11. The composition of claim 1 or claim 2, wherein said nucleic acid construct comprises a structural gene operably linked to a regulatory region.

12. The composition of claim 1 or claim 2 comprising dry powder particles, wherein the nucleic acid construct is present in the particles at a weight ratio from 1:10 to 1:500 (nucleic acid construct: particle).

13. The composition of claim 1 or claim 2, wherein said nucleic acid construct comprises plasmid DNA.

14. The composition of claim 1 or claim 2, wherein said excipient is selected from the group consisting of proteins, peptides, carbohydrates, amino acids, organic acids and their salts, and inorganic salts.

15. The composition of claim 14, wherein said excipient is serum albumin.

16. The composition of claim 1 or claim 2, wherein said powder is characterized by a dispersibility of at least about 36%.

17. The composition of claim 1 or claim 2 comprising particles having an average particle size in the range from 0.5 microns to 50 microns.

18. The composition of claim 1 or claim 2 comprising particles having a mass median aerodynamic diameter (MMAD) of less than 5 microns.

19. A method for delivery of a nucleic acid construct to the lungs of a human patient, said method comprising administering by inhalation the composition of claim 1 or claim 2 in aerosolized form.

20. A method for delivering a nucleic acid dry powder composition to a patient, said method comprising: dispersing an amount of the powder composition of claim 1 or claim 2 in a gas stream to form an aerosol, and delivering the aerosol to the lungs of said patient by inhalation.

\* \* \* \* \*